(12) United States Patent
Pratt

(10) Patent No.: US 8,024,958 B2
(45) Date of Patent: Sep. 27, 2011

(54) GAS SENSORS WITH THERMALLY INSULATING CERAMIC SUBSTRATES

(75) Inventor: Keith F. E. Pratt, Portsmouth (GB)

(73) Assignee: Life Safety Distribution AG, Uster (CH)

( * ) Notice: Subject to any disclaimer, the term of this patent is extended or adjusted under 35 U.S.C. 154(b) by 363 days.

(21) Appl. No.: 12/117,332

(22) Filed: May 8, 2008

(65) Prior Publication Data

US 2009/0120162 A1    May 14, 2009

Related U.S. Application Data

(60) Provisional application No. 60/938,748, filed on May 18, 2007.

(51) Int. Cl.
*G01N 27/16* (2006.01)
*G01N 27/12* (2006.01)
(52) U.S. Cl. ........... 73/25.03; 73/31.06; 422/95; 422/97
(58) Field of Classification Search .............. 73/23.31, 73/25.03, 31.06, 335.04; 977/953, 957; 422/84, 422/94–97
See application file for complete search history.

(56) References Cited

U.S. PATENT DOCUMENTS

| | | | |
|---|---|---|---|
| 3,978,006 A * | 8/1976 | Topp et al. | 252/408.1 |
| 5,338,416 A | 8/1994 | Mlcak et al. | |
| 5,549,871 A | 8/1996 | Kocache et al. | |
| 5,759,367 A | 6/1998 | Matsuura et al. | |
| 5,898,101 A * | 4/1999 | Lyle et al. | 73/23.2 |
| 6,303,011 B1 | 10/2001 | Gao et al. | |
| 6,352,631 B1 | 3/2002 | Bloemer et al. | |
| 6,395,230 B1 | 5/2002 | Guerin et al. | |
| 6,442,994 B1 | 9/2002 | Slater | |
| 2002/0146352 A1 | 10/2002 | Wang et al. | 422/96 |

FOREIGN PATENT DOCUMENTS

| | | |
|---|---|---|
| EP | 0 608 122 A2 | 7/1994 |
| EP | 1 160 567 | 12/2001 |
| EP | 1 114 207 | 12/2002 |
| EP | 1 403 637 A1 | 3/2004 |
| WO | WO 95 04926 | 2/1995 |
| WO | WO 97/44650 | 11/1997 |
| WO | WO 2007/026177 | 3/2007 |

OTHER PUBLICATIONS

PCT International Searching Authority, EPO, Luis-Miguel Paredes Sanchez, partial international search, mailed Jan. 28, 2009, 4 pages.
MACOR Machinable Glass Ceramic, Corning Incorporated Lighting and Materials, http://www.corning.com/docs/specialtymaterials/pisheets/Macor.pdf.
Cermet Platinum Conductor for Heating Elements and Sensors, Electro-Science Laboratories, Inc., http://www.electroscience.com/pdf/5545.pdf.
Ceraflex Ultra Thin Zirconia for Fuel Cells and Electronics, Marketech International Inc., 1996, http://www.marketech-ceramics.com/pages/cereflex.html.

* cited by examiner

*Primary Examiner* — Lisa Caputo
*Assistant Examiner* — Punam Roy
(74) *Attorney, Agent, or Firm* — Husch Blackwell

(57) ABSTRACT

A gas sensor includes a substrate having a low thermal conductivity. Localized heating can be produced using a serpentined heater carried by the substrate. The low thermal conductivity of the substrate substantially confines the generated heat to a region local to the heater thereby reducing required power to operate the sensor. Multiple sensing elements can be deposited onto the substrate adjacent to respective heaters and relatively close together because of the thermal isolation provided by the substrate. In one embodiment, the sensor can include the ceramic substrate, the heater, catalytic material overlying the heater with a gas impermeable layer overlying, at least in part the catalytic material.

14 Claims, 9 Drawing Sheets

GAS SENSORS WITH THERMALLY INSULATING CERAMIC SUBSTRATES

CROSS-REFERENCE TO RELATED APPLICATION

This application claims the benefit of the filing date of U.S. Provisional Application Ser. No. 60/938,748 filed May 18, 2007 and entitled "Gas Sensors". That Provisional Application is hereby incorporated herein by reference.

FIELD

The invention pertains to gas sensors. More particularly, the invention pertains to such sensors which incorporate ceramic substrates having low thermal conductivity.

BACKGROUND

Heated catalytic bead pellistor-type devices have been used as sensor elements in various types of detectors of combustible gases. Such devices operate by measuring heat generated by combustion of the gases. Some gases can combust rapidly within the outer regions of the devices. Others combust more uniformly within the device. In either instance, heat generated by such combustion can be sensed and measured.

One known form of pellistor includes a coiled wire heater. Such sensors can be manufactured in relatively small sizes and exhibit relatively low power consumption. However, the cost and labor involved is excessive and increases with decreasing size. Another form of pellistor has been disclosed in U.S. Pat. No. 6,395,230 B1 entitled "Pellistor", issued May 28, 2002. The '230 patent has been assigned to the assignee hereof and is incorporated herein by reference.

A number of methods have been employed to attempt to reduce the power consumption and/or manufacturing cost of pellistors. One example is the use of micromachined silicon 'hotplates' which can be made with small heated areas and hence lower power consumption. These devices have a number of disadvantages. The cost of development/redesign of micromachined silicon devices is high. The long-term stability of the heated substrate is poor at the elevated operating temperatures required (e.g., 550 degrees Celsius) and especially at the much higher temperatures required during manufacture of pellistors. The substrates are fragile, making deposition of the sensing material difficult. There are materials incompatibility issues—for example the ceramic materials normally used in pellistors (alumina/zirconia) have very different thermal expansion coefficients to substrate materials such as silicon or silicon nitride, which may result in poor adhesion and/or cracking under thermal cycling.

An alternative to silicon for microhotplates is silicon carbide, which has much better thermal stability than silicon, but can be difficult to etch. Another major disadvantage of silicon carbide is its high thermal conductivity, resulting in increased heat loss down the connecting struts of the hotplate compared with silicon/silicon nitride, giving higher power consumption for the same type of structure.

A substrate material that is commonly used for heated metal oxide gas sensors is alumina ($Al_2O_3$). Alumina has the advantages of being a much more refractory material than silicon, and is low cost and readily available. Alumina is also a commonly used substrate for screen printing, and commercial off-the-shelf screen printable metallisations and other materials compatible with alumina are readily available. Unlike silicon and silicon carbide, Alumina is difficult to micromachine on the small scales required to produce microhotplates, as it needs to be machined mechanically rather than photolithographically. Alumina is therefore typically used in the form of chips of dimensions of a few millimeters, and is typically attached to a suitable header using metal wires or lead-frames.

Alumina has a high thermal conductivity—this gives rise to a fairly uniform temperature across the device, regardless of the heater size. As a result the power consumption of such devices is excessive, and is unacceptably high compared to conventional wire-wound pellistor devices. An additional disadvantageous consequence is that the ends of the suspending wires or lead-frame connected to the sensing device are at high temperature which restricts the range of materials from which said wires or lead frame can be fabricated, and also can result in acceleration of thermally related failure modes in the wires or contacts between the wires and the substrate. In addition to having a high thermal conductivity, alumina substrates typically need to be relatively thick, for example 250 micrometers or more, in order to be sufficiently robust. This results in further lateral heat loss and hence higher power consumption. Methods have been developed to allow thermally insulated heated structures to be fabricated on alumina substrates. For example a thermally insulating glass layer can be printed between the alumina substrate and the heater+sensing layer. This approach has disadvantages. Since the glass layer is relatively thin and covers a relatively large area, heat loss is still significant. The glass layer may be less thermally stable than the underlying alumina substrate and may have a different coefficient of thermal expansion. Adhesion of the heater/electrodes/sensing material to the glass layer may be worse than to alumina. Patterning methods such as photolithography or laser trimming can be complicated by the presence of the additional layer.

It is desirable to further reduce power consumption for such gas sensors. Preferably the expenses of known coiled wire heated-type pellistors can be avoided. It is also desirable to minimize sensor poisoning.

As noted above, existing commercial catalytic bead flammable gas sensors (pellistors) are often made by winding a coil of fine platinum wire and depositing over this a relatively thick (hundreds of micrometers to several millimeters) porous catalyst/ceramic material. Larger devices generally have better poison resistance than smaller ones, this may be due to poisoning progressively destroying the activity of the sensor from the outside inwards. It is also possible that poisoning occurs at a uniform rate within the film but the target gas has a concentration profile, the steepness of which will decrease as the catalytic activity of the sensor decreases due to poisoning. In this case, a larger bead still gives improved poison resistance since the target gas is able to penetrate further into the sensor before being combusted. Whatever the mechanism, it is known that larger diameter beads typically have better poison resistance, albeit at the expense of greater power consumption.

DETAILED DESCRIPTION

Figure 1:
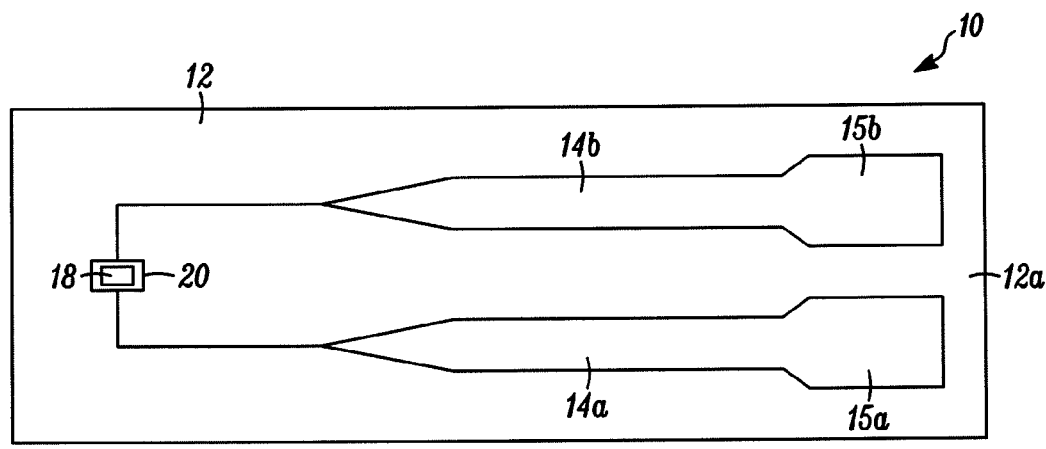
FIG. 1 is a top plan view of a sensor which embodies the present invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the invention exhibit low cost, easily manufacturable, low power consumption, rugged, reliable, reproducible, planar heated sensor substrates usable in catalytic 'pellistor' devices, heated semiconducting metal oxide sensors or any other application where traditional suspended ceramic substrates or micromachined substrates containing heaters are used. In one aspect of the invention, such substrates have low thermal conductivity but similar refractory properties to alumina. Hence, and advantageously, such sensors can be fabricated using conventional thick film processing.

In yet another aspect of the invention, small heated sensing regions can be formed on relatively large substrates. Lateral heat loss across the substrate is minimized, so only a local area of substrate gets hot. Steady state power consumption can, as a result, be reduced.

In another aspect of the invention, further reductions in power consumption can be achieved by intermittent heating. Unheated regions are at low temperature, giving better options for wire bonding and mounting. Separate heated regions formed on a single chip make it possible to form multiple gas sensing elements, for example the detector and compensator elements of a pellistor, on a single chip. Cost and complexity of fabrication can be much less than wirewound pellistors. Development/manufacturing setup cost can be much less than micromachined silicon. Thermal stability can be expected to be greatly superior to micromachined silicon devices, and may be superior to that of conventional pellistors due to the more rugged substrate. Embodiments of the invention are not limited to pellistors, but can also include semiconducting metal oxide gas sensing devices, high temperature solid state electrochemical sensors, infra red sources and any other application where a low power low cost localized heat source is required.

Embodiments of the invention can incorporate zirconia as a thermally insulating substrate material. Preferably, a form of flexible zirconia commercially vailable and manufactured by Marketech Ltd (Port Townsend, Wash., USA), under the trade name 'Ceraflex' can be used. This material has the added benefit that it can be manufactured so as to be thinner than is the case with other types of substrates. A thin substrate further reduces lateral heat loss and hence power consumption. Zirconia also has the benefit of having similar thermal expansion coefficient to the ceramic materials often used in the catalyst layer of catalytic bead devices. More preferably, zirconia can be used in a partially stabilized form (containing 3 mole percent of yttria), as this gives the optimum combination of low thermal conductivity and robustness. However, for high temperature electrochemical sensors, it may be desirable to also use the substrate as the electrolyte—in which case fully stabilized zirconia (containing 8 mole percent of yttria) is preferred.

Alternative insulating substrate materials also come within the spirit and scope of the present invention. For example aluminosilicates or magnesium silicates, which have similar thermal conductivity to zirconia though their thermal expansion coefficients, can be much lower which is likely to be a disadvantage. Low thermal conductivity machinable glass ceramics such as Macor®, manufactured by Corning Inc., New York, USA can also be considered as possible substrate materials. Any material with suitably low thermal conductivity which can be formed into a substrate compatible with conventional thick film processes can potentially be used.

Exemplary devices in accordance with the invention could, for example, be implemented with a 10.times.10 mm chip format. Serpentine heaters could be deposited on the substrate occupying areas of 0.5.times.0.5, 1.times.1 and 2.times.2 mm. The sizes of these devices are not limitations of the invention. Other embodiments could be much smaller—with heater dimensions down to a few hundred microns per side. The devices can be fabricated by conventional thick film screen printing, using, for example, a DEK1760 printer. Platinum heater ink such as ESL5545, commercially available and supplied by Agmet/Electroscience Ltd. (Reading, Berkshire, UK) can be used.

Other thick film inks may be suitable, including organometallic types, and the heater may also be deposited by other means as used in micromachined silicon type devices, such as sputtering, lift off processes etc. With a printed thick film ink, to produce heaters of sufficiently small dimensions to have power consumption comparable to or better than existing wirewound pellistors it is likely to be necessary to postprocess the printed layer by laser trimming, photolithography or other methods.

Further, in accordance with the invention, the shape of the substrate can be optimized to further reduce power consumption. The substrates can be readily produced with holes, or slots. These embodiments can provide further reductions in heat conduction and hence power consumption.

In other embodiments of the invention, the shape of the heater can be designed to produce a relatively uniform temperature over the region of interest, Alternately, a more thermally conducting material (e.g., an alumina based dielectric or a metal layer) can be deposited over the region where the temperature needs to be held uniform. The material could be deposited between the heater and substrate, over the heater, or on the opposite side of the substrate, or on both sides of the substrate.

Embodiments of the invention exhibit relatively low power requirements. In yet another aspect of the invention, multiple independent heated regions can be formed on the same substrate. This configuration is desirable and useful in implementing catalytic 'pellistor' devices. Such devices often use a matched detector and compensator, both of which could be formed on a common substrate in accordance with the invention. Independent heated regions can be formed to implement arrays of sensors each operating at a different temperature, or where a controlled temperature gradient across a single sensing material is required.

Sensors which embody the heaters of the present invention exhibit relatively low heat loss, hence lower power consumption as a result of the low thermal conductivity of zirconia. In addition, use of the thinnest possible substrates, with or without heat flow limiting openings or perforations, can also be expected to minimize heat losses. Such substrates can be bonded to an underlying support. Alternately, they can be suspended by a plurality of connecting wires.

For applications where the heater temperature needs to be accurately controlled and/or measured it is preferable to use platinum as the heater material as it can double as a platinum resistance thermometer. The heater track is preferably in some form of serpentine pattern as a simple solid block would have too low a resistance to accurately measure/control. It is also preferable for the resistance of the heater to be high compared to that of the connecting tracks leading to it, so that the heating effect is concentrated in the heater. Laser trimming can be used to produce a serpentine heater track from a solid printed block. Such processing can also be applied actively in order to trim the heater resistance to a desired value. Alternately, the heater can be deposited directly onto a substrate, screen printed or patterned by photolithography.

For gas sensing applications it is typical to add a gas sensing material, and for some types of sensors, measuring electrodes, in addition to the heater. These may also be deposited and/or patterned by screen printing or any of the techniques described above or any other technique known for the deposition of sensing materials. The materials can be deposited on the same face of the substrate as the heater or on the opposite face, or on both faces. For catalytic 'pellistor' type devices there are benefits in depositing the catalyst material directly over the heater, possibly with a thin separating barrier layer, particularly if the substrate has low thermal conductivity as heat generated by the catalyst is more readily detected by the heater than would be the case if the heater were on the opposite face of the substrate. Comparison can be made with conventional wirewound pellistors, where the heater is also in intimate thermal contact with the catalyst.

In another aspect of the invention, if a planar catalytic layer is designed such that gas only has access from the end(s) or edges of the planar layer, rather than from the top, then poisoning has to proceed through a longer distance to destroy the activity of a given amount of catalyst and/or there is a greater length available to accommodate the concentration gradient of the target gas. Thus the resulting sensor should be more poison resistant than a simple planar device, and could potentially be made more poison resistant than a conventional bead device of similar dimensions—as it is possible to produce a serpentine channel of greater length than the radius of a spherical bead of similar external size. An additional benefit of encapsulating the catalytic material may be improved mechanical resilience.

In another aspect of the invention, the layer may be covered by a gas impermeable coating, whereby gas has access via some or all of perimeter of the coating, in which case the effective 'radius' of the device is the radius of the coating. Alternately, the material may be configured in the form of a long serpentine channel.

In a different embodiment, the whole of the gas sensing catalytic layer can be encapsulated except for an entrance port or hole in the center. Advantageously, with this embodiment, the inverse radial geometry results in a larger available area for gas combustion to be made available as poisoning proceeds. This design could be used to compensate for any residual time dependent decay of sensitivity with extent of poisoning. Another embodiment could include a relatively long, straight or serpentine channel whose cross sectional area increases with distance away from the gas entrance to the channel. Thick film screen printing can be used to deposit the catalytic material and gas impermeable coating described above.

Thick film screen printing techniques are very suitable in implementing the various above described embodiments. Thick film processes are best used with ceramic substrates, especially when the device needs to be operated at elevated and/or cycled temperatures. Embodiments of the invention can be combined with low thermal conductivity ceramic substrates as described above. An additional benefit of combining a substrate with lower thermal conductivity with the long channel type of design is that controlled temperature gradients can be produced laterally along the substrate.

In other embodiments of the invention, a plurality of heaters can be formed along the length of a channel on a substrate having a low thermal conductivity. In such embodiments, the temperature due to heat generated by the reaction of gases within the vicinity of each heater can be independently measured. Advantageously, different gases can be discriminated. As discussed subsequently, effects of poisoning may also be detectable.

Further, in embodiments which include a sufficiently long channel, and multiple spaced apart heaters, an effect can be produced similar to that produced by devices which include a compensator element exposed to the gas. In these embodiments, the channel length is such that complete combustion of the ambient gases takes place before the gas comes into contact with catalytic material associated with the heater or heaters displaced furthest along the channel from a gas input or access port. As such, there is no response to the gas at that catalytic material/heater combination although that combination can be expected to respond to other ambient conditions.

Figure 2:
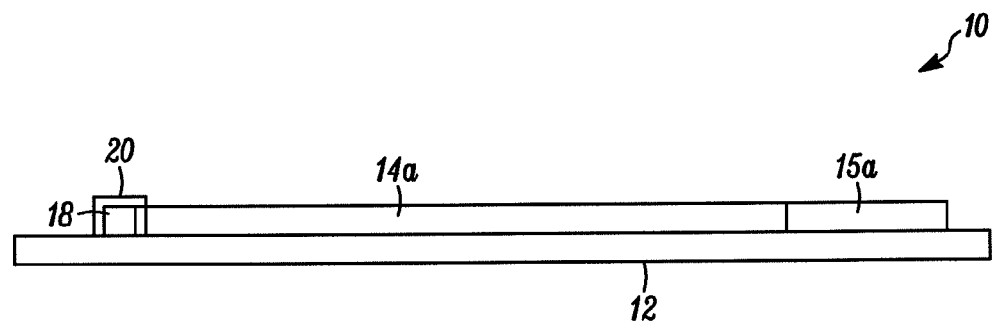
FIG. 2 is a side elevational view of the sensor of FIG. 1.
Figure 3:
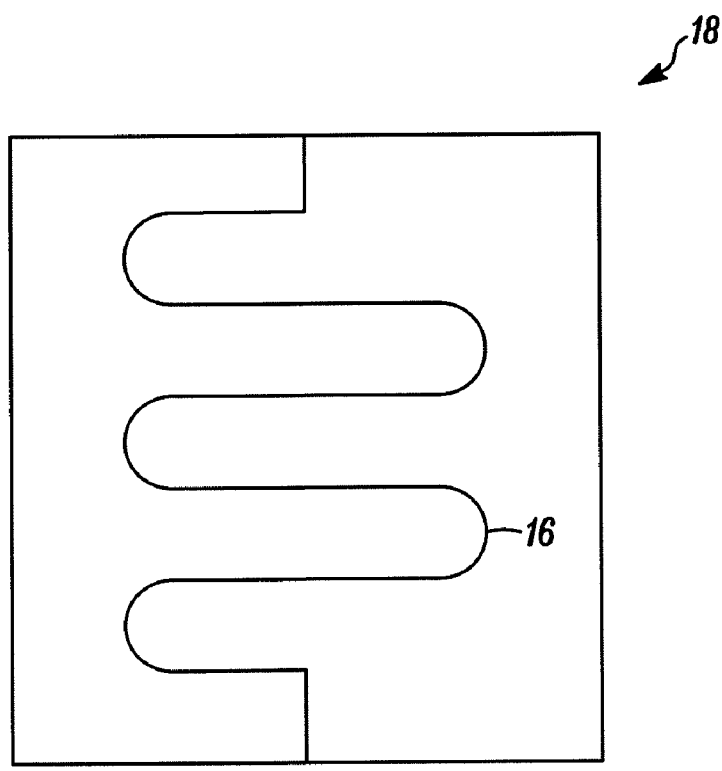
FIG. 3 is an enlarged view of a region of FIG. 1.

FIGS. 1 to 3 show one possible implementation of a catalytic gas sensor 'pellistor' demonstrating the first aspect of the invention. The substrate 12 is thermally insulating. The heater, 16, is confined to a small region, 18, of the substrate, 12, so that heating only occurs locally. Connecting tracks, 14, and connecting bond pads, 15, are required for electrical connection to the heater, 16. The design and/or material of the connecting tracks, 14, is such that heat is predominantly generated in the heater, 16, not in the connecting tracks, 14. Electrical connections to the connecting pads, 15, at the 'cold' end of the substrate (12a) may be via suitable wire bonding methods such as welding or soldering, or by connection into an 'edge connector' type of socket, or by any other means. The substrate may optionally be mechanically attached, for example by die-attach or adhesive, at the 'cold' end in the region of the connecting pads, 12a. Alternatively the device may be suspended by bond wires. For a pellistor type of sensor the catalyst, 20, may be deposited over, adjacent to, or on the opposite face, or both faces, of the substrate to the heated region, 18. For other types of sensors such as semiconducting metal oxide sensors or high temperature electrochemical sensors, additional parts such as electrodes and additional connecting tracks and pads may be required which are not shown here. FIG. 3 shows an expanded view of region 18 in FIG. 1, showing one possible layout of a serpentine heater track, 16. Region 18 may contain, in addition to the heater, a separate temperature sensing element or the heater itself may function as a temperature sensing element.

Figure 4:
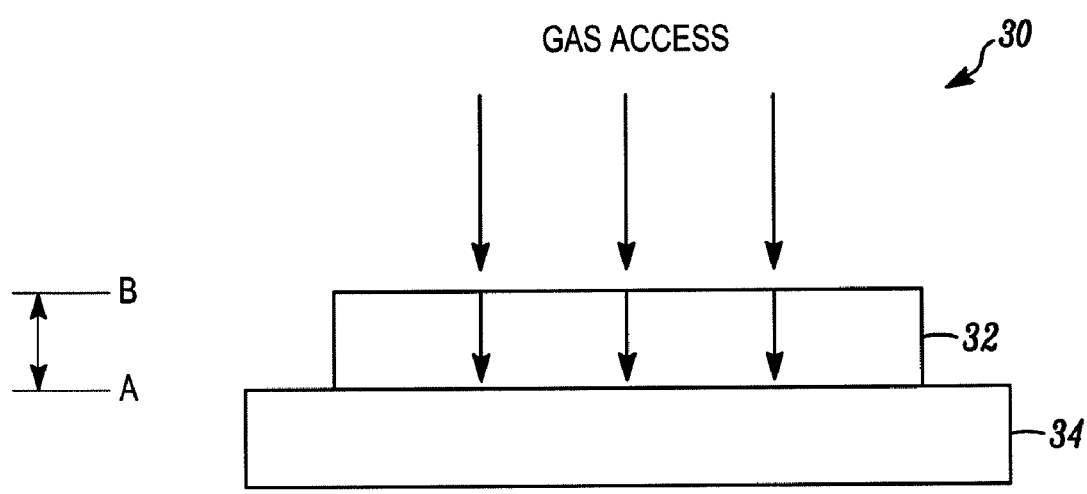
FIG. 4 is a side view of a prior art sensor.

FIG. 4 is a schematic diagram of a planar type, prior art, catalytic gas sensor 30 wherein a relatively thin A-B (e.g., 100 micrometers or less) layer of catalytic material 32 is deposited onto a substrate 34 with an integral heater. Suitable substrates include micromachined silicon/silicon carbide or ceramics. The embodiment of FIG. 4 can be subject to catalyst poisoning problems given the direct gas access to the relatively thin layer 32.

Figure 5:
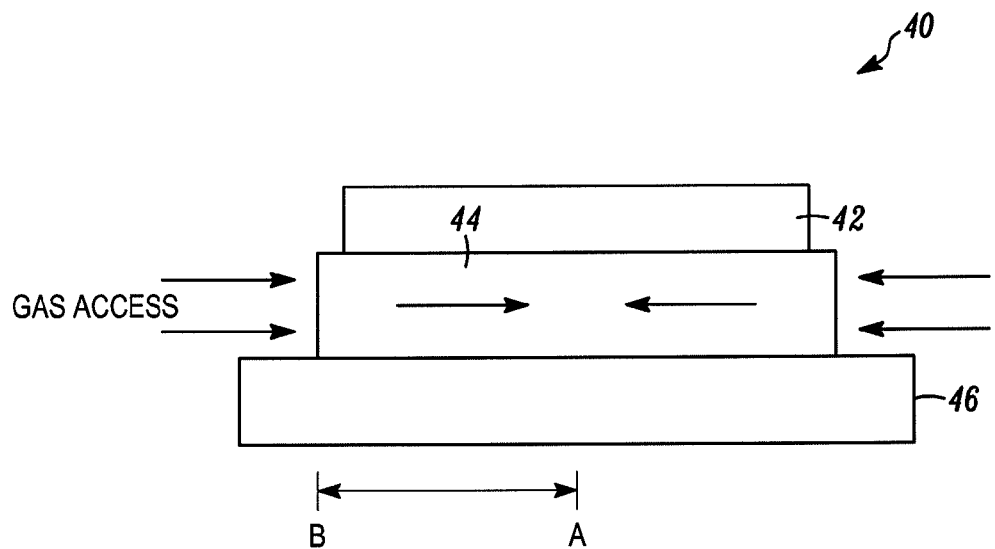
FIG. 5 is a side elevational view of another sensor which embodies the invention.

FIG. 5 illustrates one implementation of the present invention. In sensor 40, a gas impermeable layer 42 is deposited over a porous catalyst material 44 carried on a heated substrate 46.

The gas impermeable layer 42 may be, for example, a conventional dielectric or glaze material as used in thick film technology. Since gas access is now via the exposed edges of the catalyst material, the dimension A-B is now oriented in the horizontal dimension, along the substrate 46 rather than in the vertical dimension as was the case in FIG. 4. This horizontal dimension can be made much longer than the vertical dimension, using techniques such as standard thick film processing. If the catalyst material 44 is deposited in a round, cylindrical, pattern, gas can access all around its perimeter.

Figure 6:
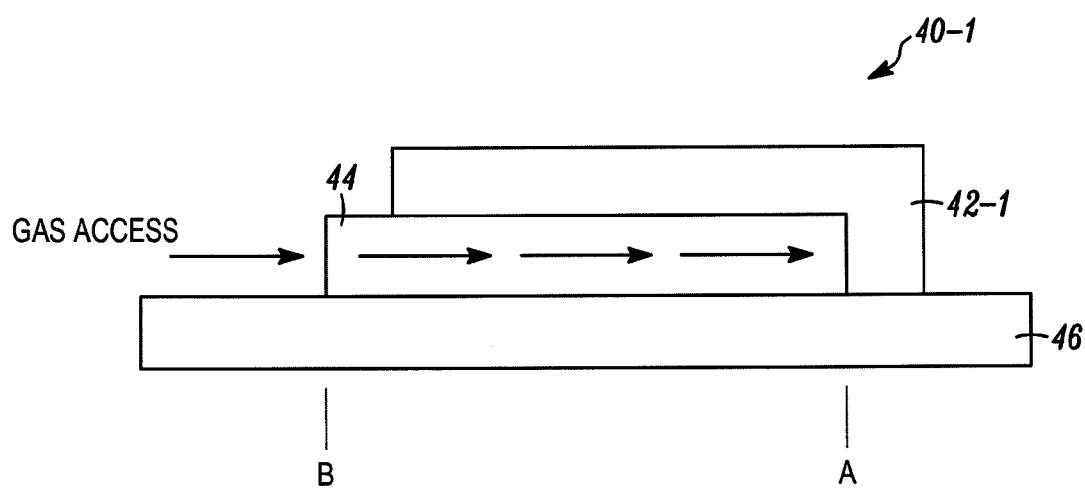
FIG. 6 is a side elevational view of another sensor which embodies the invention.

FIG. 6 illustrates another possible implementation of the present invention whereby in a sensor 40-1, the dimension A-B is approximately double that of FIG. 5 due to gas access being at one end only of catalytic layer 44 due to the blocking shape of layer 42-1. If the catalyst layer is in the form of an elongate channel then the dimension A-B is longer than is the case for the sensor of FIG. 5. There are also a number of possible implementations in between the configurations of FIGS. 5, 6—for example having multiple access points around the perimeter. All such variations come within the spirit and scope of the invention.

Figure 7A:
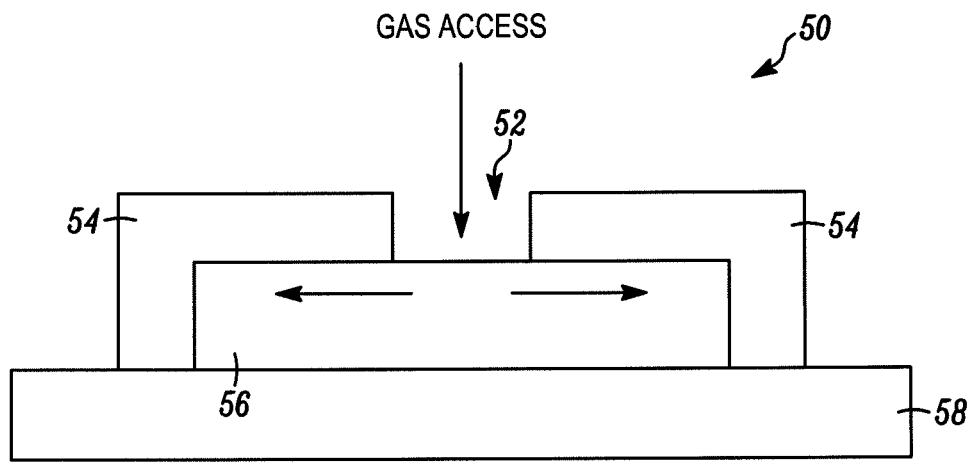
FIGS. 7A, 7B taken together illustrate yet another sensor in accordance with the invention.
Figure 7B:
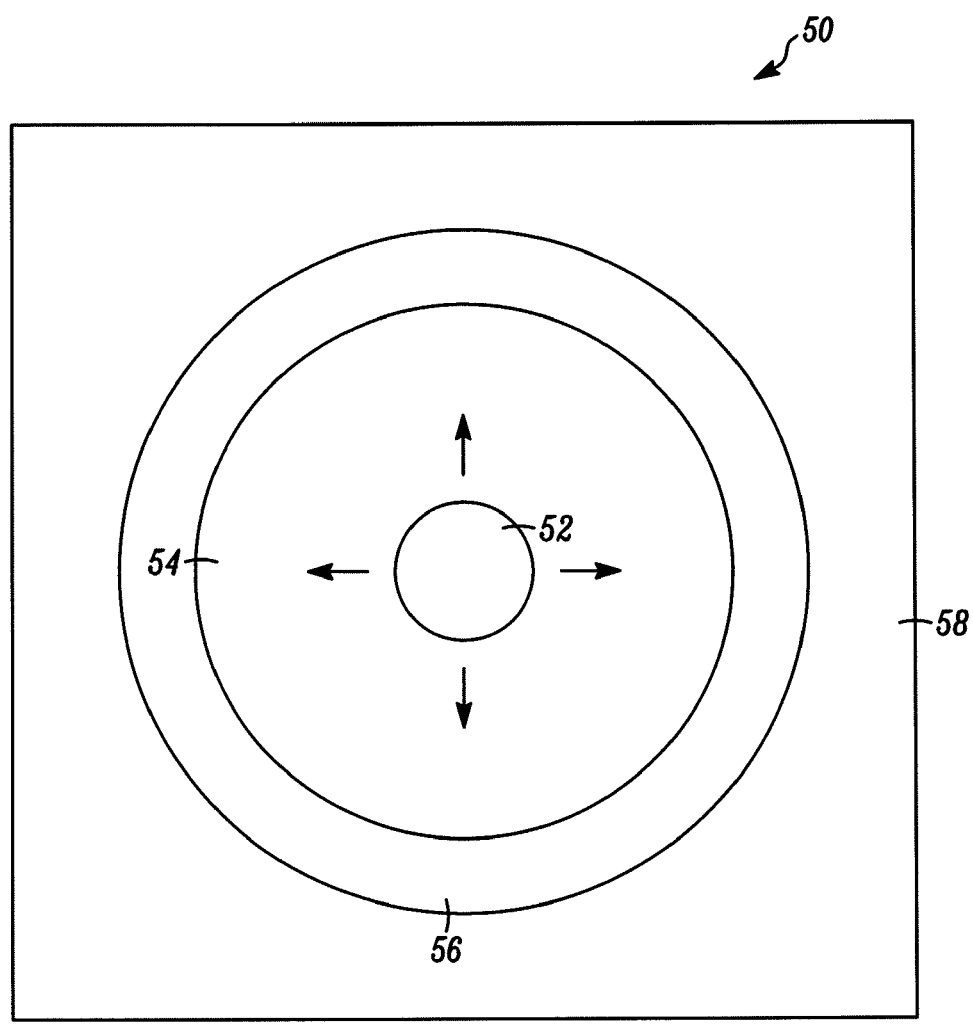

FIGS. 7A, 7B illustrate a side view and a top plan view of yet another embodiment of the invention. Here, gas access is at the centre 52 of the device 50 rather than the perimeter. Gas impermeable annular layer 54 defines port 52. Device 50 is carried on a heated substrate 58. The port configuration of FIGS. 7A, 7B may be beneficial in that the cross sectional area available for gas reaction increases as the gas diffuses further into catalytic layer 56 of the device, rather than decreasing as is the case with the conventional bead pellistors. Further benefits in terms of poison resilience, temperature/pressure dependence and repeatability may be obtained by making the access port or, opening 52 in this, or other embodiments small enough to act as a diffusion limiting capillary.

Figure 8:
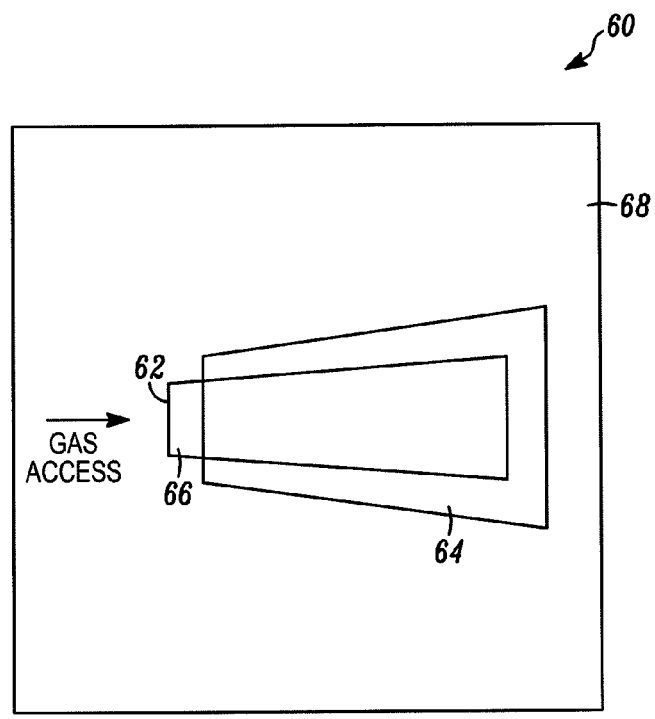
FIG. 8 illustrates yet another sensor which embodies the invention.

FIG. 8 illustrates a variant of the configuration shown in FIGS. 7A, 7B, whereby the cross sectional area available for gas reaction increases as the gas diffuses further into the device. In the sensor 60 of FIG. 8, Catalytic layer 62 tapers from a narrower access region 62 to a wider interior region. The gas impermeable layer 64 generally replicates this tapered geometry. The sensor 60 is carried on a heated substrate 68 as discussed above. Such embodiments may allow the poisoning curve to be further optimized by maximizing the plateau region of the curve.

Figure 9A:
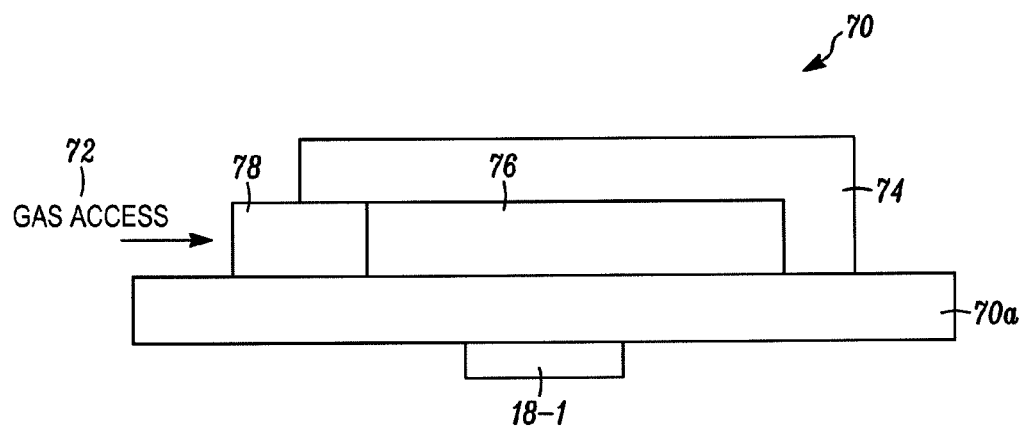
FIGS. 9A and 9B illustrate yet other variations of the invention.
Figure 9B:
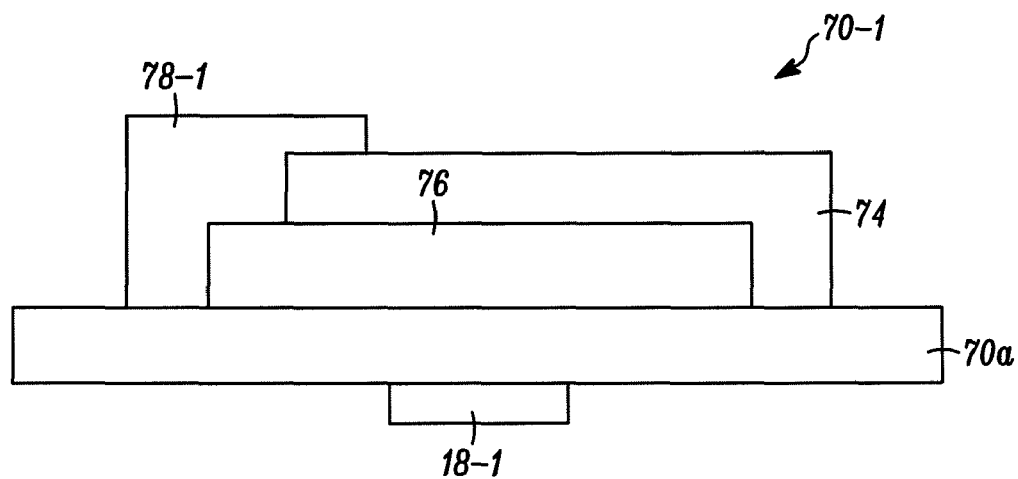

FIGS. 9A, 9B illustrate two different embodiments 70, 70-1 which include a protective layer 78, 78-1. In FIG. 9A, the protective material 78 is effectively added as an extension of the catalyst channel 76. Layer 74 is a gas impermeable layer. Sensors 70, 70-1 are carried on heated substrate 70a.

In FIG. 9B, the protective layer 78-1 is intended to have a large outer surface area to minimize the risk of blockage by, for example, exposure to dust or to short high concentrations of organosilanes which may physically block access to gas rather than 'poisoning' reactive sites in the conventional manner. Alternately, such methods of applying protective layers may also be used with any of the other embodiments shown herein. The protective layer may even completely cover the device. Heater region 18-1 is comparable to heater region 18 and heater 16 of FIG. 3.

In FIG. 9A, the catalytic 'pellistor' material 76 is deposited over a substrate 70a. Gas access to the catalytic material 76 is restricted by the gas impermeable material 74. In this implementation only a single heater region 18-1, is required.

The optional protective gas permeable material 78, may be included to protect the catalytic material 76 from poisoning or contamination or to remove interferent gases in a similar manner to protective layers used on conventional bead pellistors. The protective material 78, may also optionally partially cover the gas impermeable material 74 as in FIG. 9B.

Figure 10:
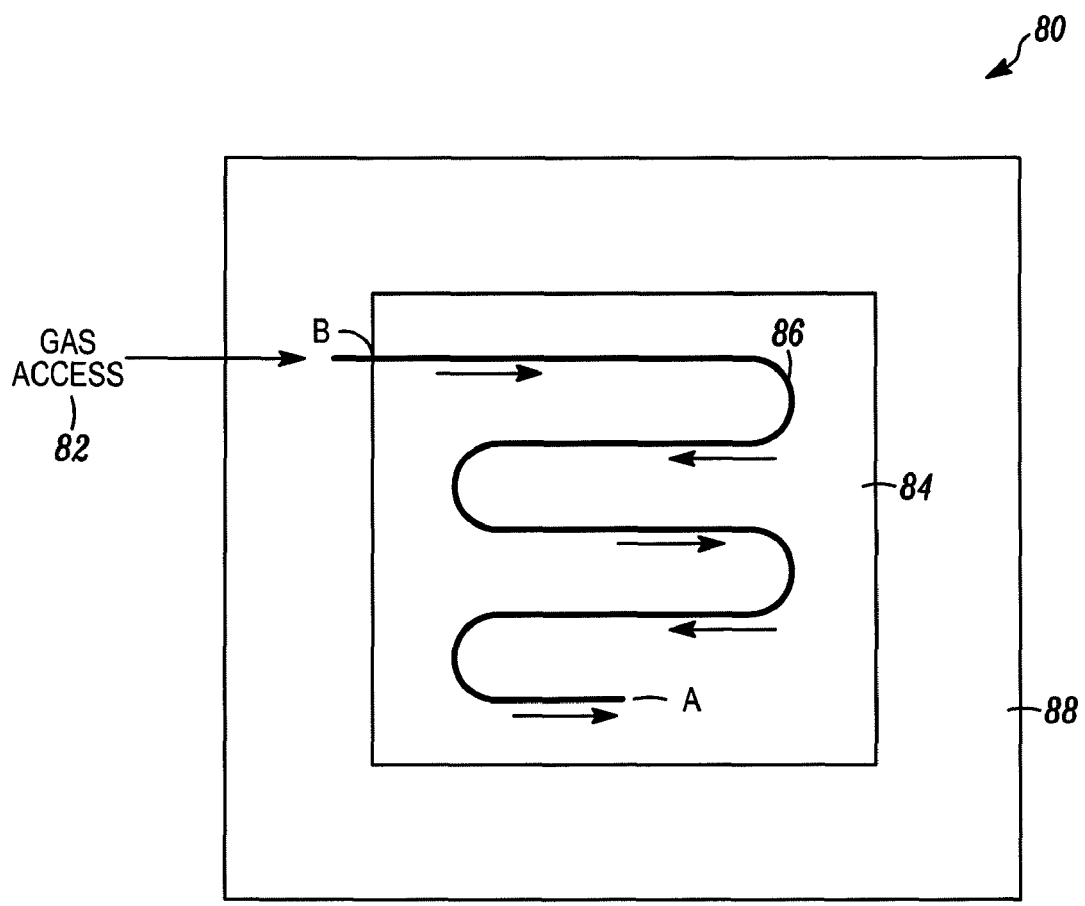
FIG. 10 illustrates a serpentine channel of catalyst material.

FIG. 10 illustrates how an elongated gas diffusion channel 86 of catalytic material such as those shown in FIG. 6, 8, or 9A, 9B may be formed with a characteristic length (A-B) greater than the physical dimensions of the sensor's substrate 88, since the characteristic length (A-B) is the length of the serpentine channel rather than a simple linear dimension. Channel 86 is covered by gas impermeable layer 84 and is carried on the heated substrate 88.

Figure 11:
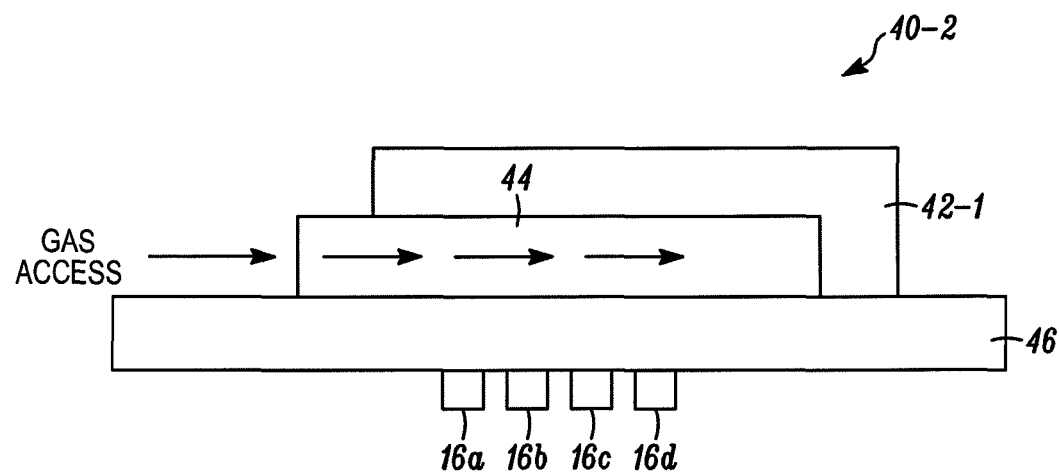
FIGS. 11 and 11A illustrate multi-heater embodiments of the invention.
Figure 12:
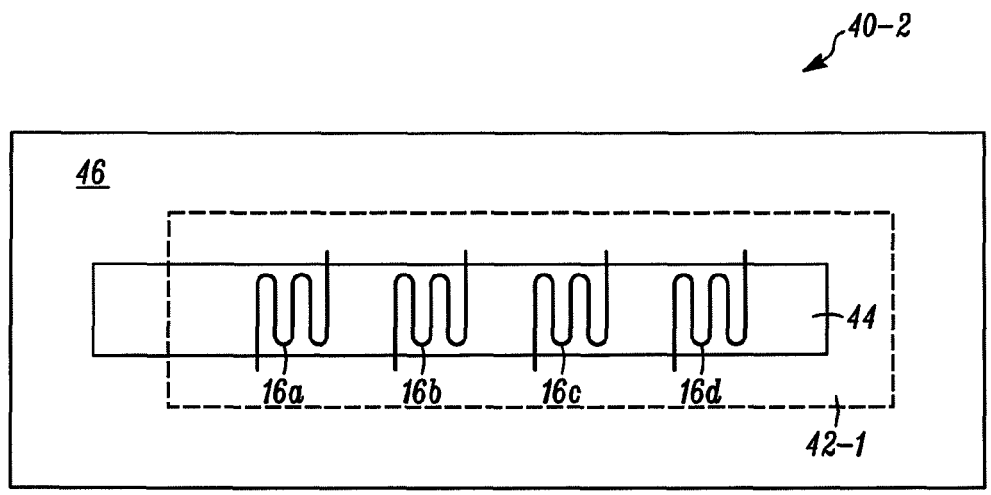
FIG. 12 illustrates a top view of multiple heaters of a type usable in the sensors of FIGS. 11, 11A.

One possible embodiment of the invention is illustrated in FIG. 11. A long channel of catalytic 'pellistor' material is encapsulated such that gas access is from one end only, as discussed above, see FIG. 6. The device is fabricated on a substrate 46 with low thermal conductivity also as discussed above. A plurality of heaters 16a, 16b . . . 16d is positioned along the length of the channel 44, as illustrated in the top view of FIG. 12. The members of the plurality of heaters 16a . . . 16d can be independently monitored/controlled and preferably being maintained at known temperatures while their individual power dissipations are measured. The channel of catalyst material is not necessarily linear but may be in the form of any of the structures described in FIGS. 5 to 10.

Figure 11A:
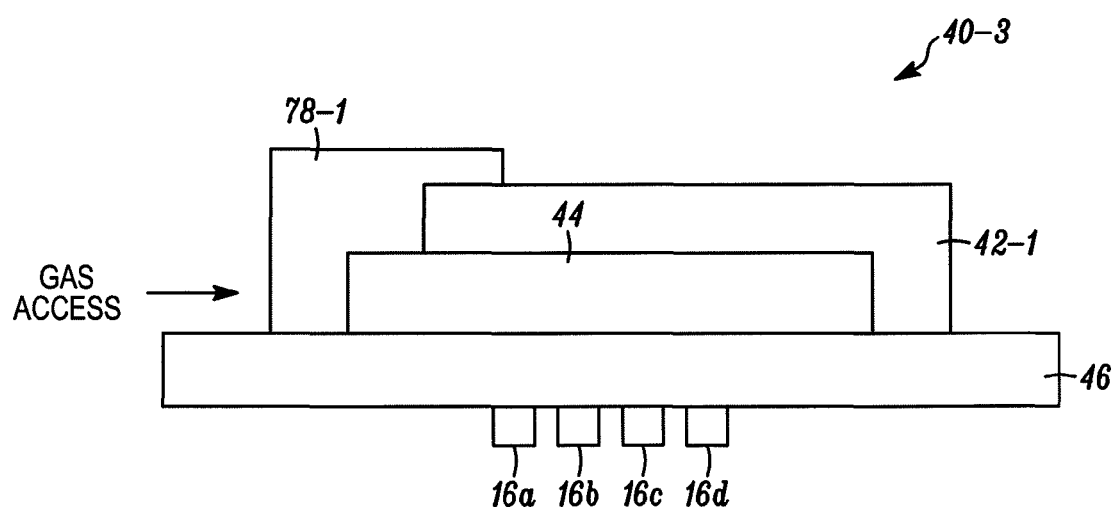

FIGS. 11, 11A illustrate embodiments where advantage can be taken of the low thermal conductivity properties of the substrate 46. The plurality of heaters 16a . . . 16d enables independent measurement of heat generated by gas reaction with the catalytic material 44 along its length, and may optionally also be used to vary the temperature along the length of that material.

Figure 13:
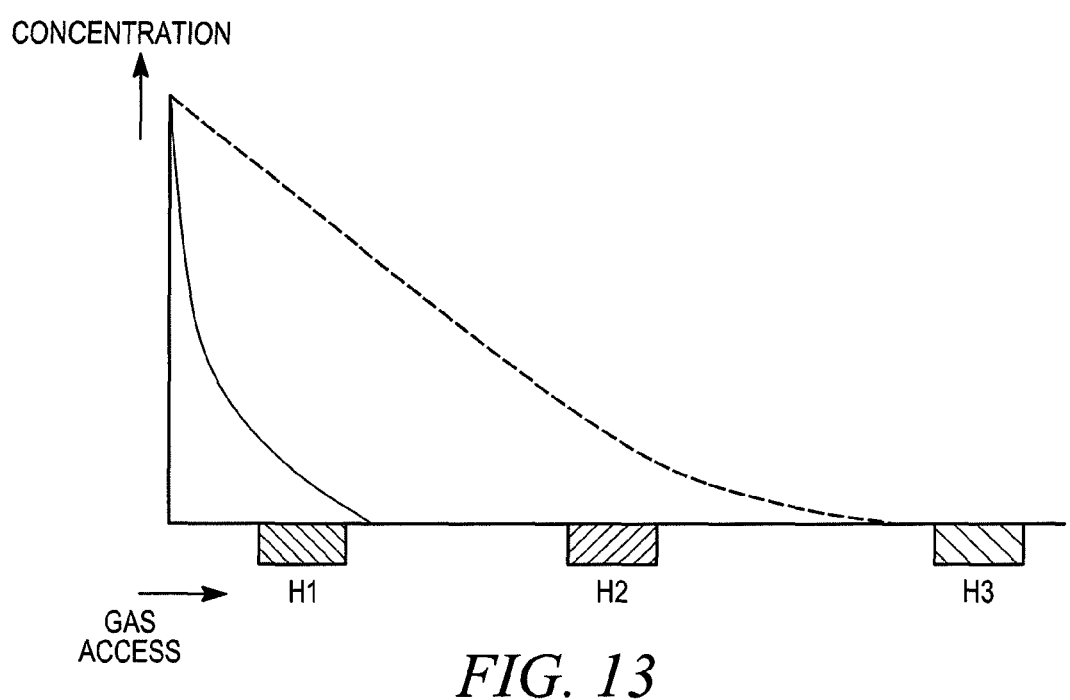
FIG. 13 is an exemplary graph of concentration vs. gas access relative to various heaters.

The above described embodiments can be used in a number of ways. FIG. 13 illustrates the expected effect of exposure to two gases having different rates of combustion. In the example of FIG. 13, the solid line shows a more reactive gas which combusts and gives a response mainly in the region of heater H1. The dashed line shows a less reactive gas which combusts less readily giving some response on heater H2 as well as on H1.

FIG. 13 can also represent the effect of poisoning on a single target gas, assuming the model whereby poisoning occurs uniformly throughout the channel but the resulting loss in catalytic activity causes the concentration gradient of gas to become less steep. The device can discriminate between changes in response due to changes in gas concentration or changes in response due to poisoning of gas response—poisoning results in a relatively higher fraction of the gas reaching, and reacting on, the inner heaters.

Figure 14:
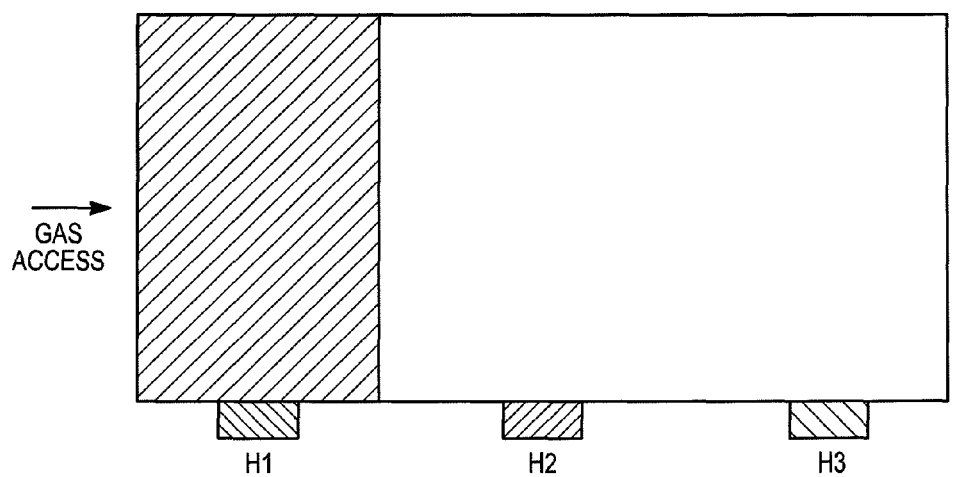
FIG. 14 is an exemplary diagram of sensor poisoning.

FIG. 14 illustrates the expected effect of poisoning on a single target gas, assuming an alternative model whereby poisoning occurs from the outer end of the channel inwards, but where there is not necessarily a significant concentration gradient of target gas. Here, gas sensitivity tends to be lost in the outer regions—indicated by the shaded region which is assumed to be poisoned. Gas sensitivity will still be observed in the unpoisoned inner regions (assuming that poisoning does not physically block gas access to the inner regions—which is unlikely in realistic conditions). Again, the device can discriminate poisoning from changes in gas concentration. In practice actual sensor performance may be some-where between the two extremes exemplified by FIG. 13 and FIG. 14, but the device will still be able to discriminate poisoning from gas response, with appropriate signal processing.

Since one can measure the extent of poisoning using this approach one can, for example, apply a correction to the signal to compensate for signal losses due to poisoning and/or provide an early warning of impending failure—this has the advantage that during a bump test, rather than simply checking that the gas response exceeds a certain value one can actually measure the extent of poisoning. This measurement does not require an accurate gas concentration but simply the presence of the correct target gas. Effectively, it is possible to discriminate between a low response due to low gas concentration, and a low response due to poisoning.

In another aspect of the invention, a heater can be provided which is sufficiently far away from the gas access end of the channel that combustible gases will not reach it. This heated region can therefore behave like a conventional compensator.

In practice one may combine the above effects by having many heaters along the length to produce poisoning detection, gas discrimination and/or compensation along a single channel—for example heater H3 in FIG. 13 could be the 'compensator' region. One could also beneficially set different regions of the device to different temperatures, adjusting the combustion kinetics of different gases. Varying the temperature(s) during gas measurement can produce further information based on the differing concentration profiles, due to differing Arrhenius temperature dependences of combustion rates of different gases, further enhancing selectivity and gas identification. Transient temperature changes can be used to discriminate rates of combustion and diffusion.

The invention is not however restricted to pellistors but can also be used in connection with other types of sensors. All such variations come within the spirit and scope of the invention.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A gas sensor comprising:
a planar substrate;
a heater carried by the substrate;
a temperature sensor that detects a temperature of the substrate proximate the heater;
a catalyst carried by the substrate, the catalyst exhibiting a predetermined first area; and
a gas impermeable layer formed adjacent to the catalyst, the layer defines a predetermined gas inflow region on the catalyst with the inflow region having a second area a predetermined amount less than the first area,
wherein the whole of the catalyst is encapsulated by the substrate and gas impermeable layer,
wherein an outside surface except for the gas inflow port is completely covered and in continuous direct contact with at least one of the substrate and gas impermeable layer,
wherein the layer overlays the catalyst and defines one of, an annular gas inflow region, a gas inflow region formed as an area on an edge of an elongated catalyst, or a gas inflow region formed as an area on a selected surface of the catalyst, and
wherein at least a portion of the inflow region is covered by a selected protective layer.

2. A sensor as in claim 1 where the catalyst has one of a cylindrical cross section, or, a substantially polygonal cross section.

3. A sensor as in claim 1 where the substrate comprises a relatively low thermal conductivity material which carries a heater adjacent to the catalyst.

4. A sensor as in claim 3 where the substrate comprises zirconia.

5. A sensor as in claim 1 where the catalyst exhibits an elongated serpentined body portion.

6. A sensor as in claim 5 where the inflow region is defined as an end surface of the serpentined body portion.

7. A sensor as in claim 6 where the serpentined body portion has a predetermined length greater than a length parameter of the substrate.

8. A gas sensor comprising:
a planar substrate;
a heater carried by the substrate;
a temperature sensor that detects a temperature of the substrate proximate the heater;
a catalyst carried by the substrate, the catalyst exhibiting a predetermined first area; and
a gas impermeable layer formed adjacent to the catalyst, the layer defines a predetermined gas inflow region on the catalyst with the inflow region having a second area a predetermined amount less than the first area,
wherein the whole of the catalyst is encapsulated by the substrate and gas impermeable layer,
wherein an outside surface except for the gas inflow port is completely covered and in continuous direct contact with at least one of the substrate and gas impermeable layer,
wherein the layer overlays the catalyst and defines one of, an annular gas inflow region, a gas inflow region formed as an area on an edge of an elongated catalyst, or a gas inflow region formed as an area on a selected surface of the catalyst, and
wherein the catalyst exhibits an elongated serpentined body portion.

9. A sensor as in claim 8 where the catalyst has one of a cylindrical cross section, or, a substantially polygonal cross section.

10. A sensor as in claim 8 where the substrate comprises a relatively low thermal conductivity material which carries a heater adjacent to the catalyst.

11. A sensor as in claim 10 where the substrate comprises zirconia.

12. A sensor as in claim 8 where at least a portion of the inflow region is covered by a selected protective layer.

13. A sensor as in claim 8 where the inflow region is defined as an end surface of the serpentined body portion.

14. A sensor as in claim 13 where the serpentined body portion has a predetermined length greater than a length parameter of the substrate.

* * * * *